United States Patent [19]

Fuess

[11] Plant 3,999

[45] Dec. 28, 1976

[54] CHRYSANTHEMUM PLANT

[76] Inventor: Janet A. Fuess, 901 Red Hill Road, New Hartford, N.Y. 13413

[21] Appl. No.: 646,177

[22] Filed: Jan. 2, 1976

[51] Int. Cl.[2] ..... A01H 5/00
[52] U.S. Cl. ..... Plt./74
[58] Field of Search ..... Plt./74, 75

*Primary Examiner*—Robert E. Bagwill
*Attorney, Agent, or Firm*—Donald D. Jeffery

CLAIM

A new and distinct cultivar of chrysanthemum plant known by the cultivar name White Stardom and particularly characterized by the combined characteristics of daisy inflorescence type; white ray floret color; diameter across face of inflorescence of 1.75 inches up to 2.25 inches when fully expanded; a natural season flowering date of September 25; relatively compact growth habit with good spread; prolific flowering; response period of approximately 7 weeks, and excellent keeping quality.

1 Drawing Figure

1

The present invention comprises a new and distinct cultivar of *Chrysanthemum morifolium*, hereinafter referred to by the cultivar name White Stardom. White Stardom is a mutation of the patented cultivar Stardom, disclosed in U.S. Plant Pat. No. 3,530, granted Mar. 19, 1974.

White Stardom was discovered on Sept. 2, 1974 in a cultivated garden in New Hartford, N.Y. as a mutation in a flowering crop of chrysanthemums of the parent cultivar Stardom. Asexual reproduction of White Stardom was first initiated by cuttings taken Oct. 23, 1974, and such asexual reproduction has demonstrated that the characteristics as herein disclosed for White Stardom are firmly fixed and are retained through successive generations of asexual reproduction.

All of the presently known characteristics of White Stardom are similar to those of the parent cultivar Stardom, except for the white flower color of White Stardom as contrasted to the generally light lavender flower color of Stardom. The following characteristics in combination distinguish White Stardom as a new and distinct cultivar:

1. Flowers which are approximately 1.75 inches in diameter up to 2.25 inches in diameter when fully expanded.
2. Use as a garden chrysanthemum having daisy inflorescence type.
3. White ray floret color.
4. A relatively early natural season flowering date of approximately September 25.
5. A relatively compact growth habit with good spread.
6. Excellent keeping quality.
7. A response period of approximately 7 weeks.
8. Prolific flowering.

The following detailed description of White Stardom is based on observations made of the new cultivar both in New Hartford, N.Y. and in Barberton, Ohio. The response time, blooming period, color and total vigor may vary significantly with varying environmental conditions such as temperature, daylength, and light intensity. Suggested flowering in the northern and western United States is from April through May and September through October; in Florida, January through February.

2

The accompanying photographic drawing shows the unique characteristics of the new cultivar, the color being as nearly true as possible with color illustrations of this type. The drawing comprises a comparison color photograph, with White Stardom appearing on the left and the parent cultivar Stardom on the right. In the description which follows, color references are made to the Munsell Color Book, 1963 edition.

Botanical Classification: *Chrysanthemum morifolium.*

Inflorescence:
- *Diameter across face.*—1.75 to 2.25 inches.
- *Borne.*—Cluster on elongated pedicels.
- *Stems.*—Wiry.
- *Form.*—Daisy.
- *Permanence.*—10–14 days.
- *Color.*—Disc Florets: Yellow green, 8.75 Y/7/12 to dark yellow, 1.25Y7/4. Ray Florets: White.
- *Texture of ray florets.*—Smooth.
- *Appearance and form of ray florets.*—Closed at base, broadening rapidly to a wide, flat keel, tapering quickly to a notched rounded tip.
- *Arrangement.*—Composite, whorled on a single receptacle.
- *Persistence.*—Resists shatter.
- *Fragrance.*—Typical chrysanthemum.

Reproductive organs:
- *Stamen, anthers.*—150–200.
- *Pollen.*—None to abundant (functional sterility).
- *Arrangement.*—Clustered in center of flower, if present.
- *Styles.*—Present both ray and disc florets.
- *Length.*—Short.
- *Ovaries.*—At the base of petal attached to receptacle.

PLANT

Form: Herbaceous.

Growth: Compact, spreading.

Height: Approximately 11 inches when flowered naturally as field grown plants from a planting made in mid-June and given a single pinch in late June.

Spread: Approximately 12 inches when flowered naturally as filed grown plants from a planting made in mid-June and given a single pinch in late June.

Foliage:

*Top side.*—Dark green, 7.5GY4/4.
*Size.*—3.25 inches long, 2 inches wide.
*Quantity.*—Numerous.
*Shape.*—Spatulate lobed.
*Texture.*—Coarse.
*Ribs and veins.*—Prominent.
*Edge.*—Moderately indented.
*Serration.*—Moderate.
*Under side.*—Light green, 7.5GY5/4.
*Stipules.*—Rudimentary.

I claim:

1. A new and distinct cultivar of chrysanthemum plant known by the cultivar name White Stardom and particularly characterized by the combined characteristics of daisy inflorescence type; white ray floret color; diameter across face of inflorescence of 1.75 inches up to 2.25 inches when fully expanded; a natural season flowering date of September 25; relatively compact growth habit with good spread; prolific flowering; response period of approximately 7 weeks, and excellent keeping quality.

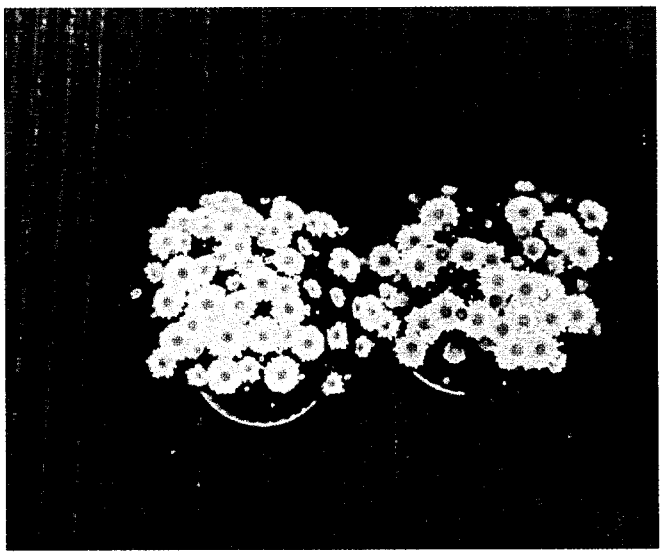

* * * * *